(12) United States Patent
Rydgren

(10) Patent No.: US 6,874,503 B2
(45) Date of Patent: Apr. 5, 2005

(54) FLUID FLOW REGULATION SYSTEM

(75) Inventor: Goran Rydgren, Bunkeflostrand (SE)

(73) Assignee: Maquet Critical Care AB, Solna (SE)

( * ) Notice: Subject to any disclaimer, the term of this patent is extended or adjusted under 35 U.S.C. 154(b) by 83 days.

(21) Appl. No.: 10/180,578

(22) Filed: Jun. 25, 2002

(65) Prior Publication Data

US 2003/0005932 A1 Jan. 9, 2003

(30) Foreign Application Priority Data

Jul. 4, 2001 (SE) .............................................. 0102400

(51) Int. Cl.$^7$ .......................................... A61M 16/00
(52) U.S. Cl. ........................... 128/205.24; 128/204.18; 128/203.12; 128/204.21; 137/115.05; 137/118.04
(58) Field of Search ...................... 137/115.05, 118.04; 128/204.18, 204.21, 204.26, 205.14, 205.19, 202.22, 203.12

(56) References Cited

U.S. PATENT DOCUMENTS

| | | | | | |
|---|---|---|---|---|---|
| 4,239,039 A | * | 12/1980 | Thompson | ............. | 128/205.24 |
| 4,259,968 A | * | 4/1981 | Rodder | ........................ | 600/537 |
| 4,262,689 A | * | 4/1981 | Rodder | .................. | 137/246.12 |
| 4,333,453 A | * | 6/1982 | Rodder | .................. | 128/205.24 |
| 4,463,756 A | * | 8/1984 | Thuc | ..................... | 128/204.21 |
| 4,819,693 A | * | 4/1989 | Rodder | .................... | 137/625.4 |
| 4,957,107 A | * | 9/1990 | Sipin | ..................... | 128/204.21 |
| 4,967,783 A | * | 11/1990 | Loos | ..................... | 137/115.05 |
| 4,989,597 A | * | 2/1991 | Werner | .................. | 128/203.12 |
| 5,092,326 A | * | 3/1992 | Winn et al. | ............ | 128/205.13 |
| 5,148,802 A | * | 9/1992 | Sanders et al. | ........ | 128/204.18 |
| 5,150,291 A | * | 9/1992 | Cummings et al. | ..... | 128/204.23 |
| 5,507,282 A | * | 4/1996 | Younes | .................. | 128/204.21 |
| 5,537,993 A | | 7/1996 | Reichert et al. | | |
| 5,542,416 A | | 8/1996 | Chalvignac | | |
| 6,595,213 B2 | * | 7/2003 | Bennarsten | ............ | 128/205.19 |

FOREIGN PATENT DOCUMENTS

| | | |
|---|---|---|
| EP | 0 813 883 | 12/1997 |
| EP | 0 862 922 | 9/1998 |
| WO | WO 01/41856 | 6/2001 |

* cited by examiner

Primary Examiner—Henry Bennett
Assistant Examiner—Mital Patel
(74) Attorney, Agent, or Firm—Schiff Hardin LLP

(57) ABSTRACT

A fluid flow regulation system has an inlet, an outlet, and an adjustable flow regulator connected between the inlet and the outlet. The regulator has a closed position at which a leakage gas flow through the system is established. An extraction device is provided for fluid connection with one or both of the inlet and the outlet and is operable to extract fluid to provide a zero or negative flow from the outlet when the flow regulator is in the closed position.

5 Claims, 2 Drawing Sheets

FLUID FLOW REGULATION SYSTEM

BACKGROUND OF THE INVENTION

1. Field of the Invention

The present invention relates to a fluid flow regulation system and in particular to a fluid flow regulation system for regulating a gas flow, especially of an additive gas, in a patient breathing circuit of a mechanical breathing aid.

2. Description of the Prior Art

A known fluid flow regulation system has a valve arrangement with an inlet flow path which terminates in a valve opening, an outlet flow path in fluid connection with the valve opening and a sealing element which co-operates with the valve opening to provide an adjustable regulation of flow through the valve arrangement. The sealing element is movable to a closed position in which it presses against the valve opening to seal it against fluid through-flow and to an open position in which it is displaced from the valve opening to establish a desired through-flow which is adjustable by varying the amount of displacement relative to the valve opening. It is also known to employ such a system to regulate the delivery of small amounts of an additive gas into a breathing gas for supply to a patient. In this arrangement the inlet flow path is connected to a supply of the additive gas and the outlet flow path is connected to an inspiration side of a patient breathing circuit which is intended to provide a gas flow path between a mechanical breathing aid, such as a ventilator, respirator or anaesthetic device, and a patient's airways.

A problem with this known regulation system concerns the sealing element of the valve arrangement. If the part of the element which seals against the valve opening is formed of a rigid material, then small desired flows may be accurately established but a proper sealing in the closed position is difficult to achieve and a leakage flow prevails even in the closed position. However, if a less rigid, resiliently deformable, material is used for that part of the sealing element, a fluid tight seal can be established in the closed position since the element can more readily be deformed to the shape of the valve opening, but small flows can be less accurately established because of a hysteretic effect in the displacement of the sealing element caused by the sealing element having to regain its original shape before it moves away from the valve opening.

SUMMARY OF THE INVENTION

It is an object of the present invention to provide a fluid flow regulation system, and a breathing apparatus employing such a fluid flow regulation system, wherein the aforementioned problems associated with known systems of this type are avoided.

This object is achieved in accordance with the principles of the present invention in a fluid flow regulation system having an inlet and an outlet with an adjustable flow regulator connected between the inlet and the outlet, the flow regulator having a closed position at which a leakage gas flow between the inlet and the outlet occurs, and further having an extraction device in fluid communication with one or both of the inlet and the outlet, which is operable to extract fluid to provide at most a zero flow from the outlet when the flow regulator is in the closed position.

When this fluid flow regulation system is used in a patient breathing arrangement, the inlet can receive additive gas from an additive gas flow path, and the outlet can supply the received additive gas to the inspiration side of the patient breathing circuit in the breathing arrangement.

Thus the problem associated with the known regulation system is mitigated by using a flow regulation arrangement which is configured to establish, in a closed position, a leakage through-flow in co-operation with an extraction device, such as a suction pump, arranged in fluid communication with one or other of the inlet or the outlet of the system and operable to actively extract fluid, at least when the flow regulation means is in the closed position, in an amount to provide a zero flow from the outlet.

DESCRIPTION OF THE PREFERRED EMBODIMENTS

Figure 1:
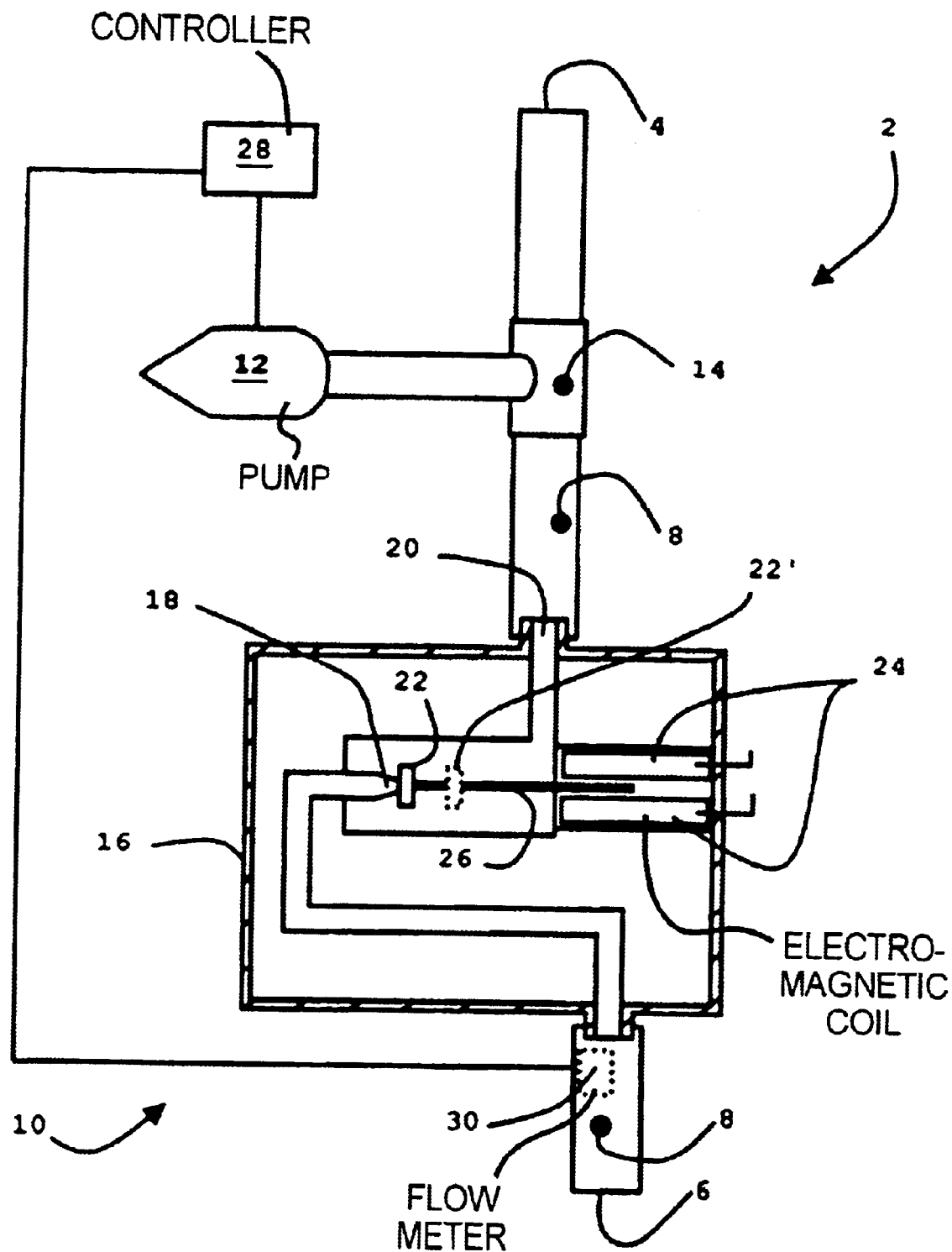
FIG. 1 is a schematic illustration of a fluid flow regulation system according to the present invention

In FIG. 1 a fluid flow regulation system 2 is shown which has an inlet 4 and an outlet 6 arranged at opposite ends of a fluid conduit 8 to delimit a flow path through the system 2. Also included in the system 2 is a valve arrangement 10, connected inline with the conduit 8 and an extraction device, here a pump 12, in fluid communication with conduit 8 via a "T-Piece" connector 14, which in the present embodiment is shown located between the valve arrangement 10 and the inlet 4. In another arrangement (not shown) the T-Piece connector 14 may be placed additionally or alternatively in fluid communication with the conduit 8 at a location between the valve arrangement 10 and the outlet 6 of the system 2. It will be appreciated that the pump 12 may even be connected directly at or within the valve housing 16 and the conduit 8 dispensed with as part of the fluid flow regulation system 2 without departing from the inventive concept.

The valve arrangement 10 is here illustrated as a conventional electromagnetic valve and will only be described in sufficient detail to enable an understanding of the principles of the present invention. Inside of a valve housing 16 of the valve arrangement 10 a valve opening 18 is located which is arranged for fluid communication with the inlet 4 of the system 2 and with an outlet 20 of the housing 16. A movable sealing element 22 is cooperably arranged with the valve opening 18 such that in an open position (illustrated by the broken lines 22') the opening 18 is unblocked and fluid a desired flow can be established from the inlet 4 of the system 2 and through the outlet 20 of the housing 16 and in a closed position (as here illustrated by the solid lines) is moved towards the valve opening 18 to establish a leakage flow from the inlet 4 of the system 2 and through the outlet 20 of the housing 16. Movement of the sealing element 22 to the open and the closed positions is effected in a conventional manner by energization of an electromagnetic coil arrangement 24 which surrounds a magnetically susceptible portion of a actuator rod 26, connected to the sealing element 22. Thus the position of the sealing element 22 with respect to the valve opening 18 is controlled by regulating a current through the coil arrangement 24 using a variable current supply unit (not shown). In the present embodiment the sealing element 22 is formed, at least in a region corresponding to the valve opening 18, of a rigid material and the closed position is when the element 22 is urged against the valve opening 18.

If an elastically deformable material is used instead of the rigid material then the closed position is when the element 22 is located relative to the valve opening 18 without the element being deformed such that a small flow, being the leakage flow, is established. In this manner positional hysteresis caused by the deformation of the sealing head 22 when it is urged against the valve opening 18 may be avoided.

The pump 12 is connected to a controller 28 which regulates the power to the pump 12 is dependence of a signal from a flow meter 30 disposed to measure fluid flow from the outlet 6 of the system 2 and in the present example is disposed in the conduit 8 which connects the outlet 20 of the valve arrangement means 10 to the outlet 6 of the system 2. The controller 28 of the present embodiment regulates the power to cause the pump 12 to extract fluid from the conduit 8, via the T-piece 14 at a rate such that zero flow from the outlet 6 is measured by the flow meter 30 when the sealing element 22 is in the closed position. This may be detected by the flow meter 30 which can be arranged to cooperate with the controller 28 to provide power to the pump 12 only when the measured flow falls below a predetermined level, selected to indicate a closing of the valve arrangement 10. Indeed the pump 12 may be regulated to establish a negative flow from the outlet 6. In this regime fluid then flows in the reverse direction; from beyond the outlet 6, through the valving means 10 and toward the inlet 4; to advantageously flush the regulating system 2. Thus any fluid remaining in the system 2 when the sealing element 22 is in the closed position may be replaced with fluid from beyond the outlet 6.

In a simplified embodiment the pump 12 may be set to continuously extract fluid from the conduit 8 at a rate at least that of an expected maximum leakage flow to prevent flow of fluid from the system 2 when the sealing element 22 is in the closed position.

Figure 2:
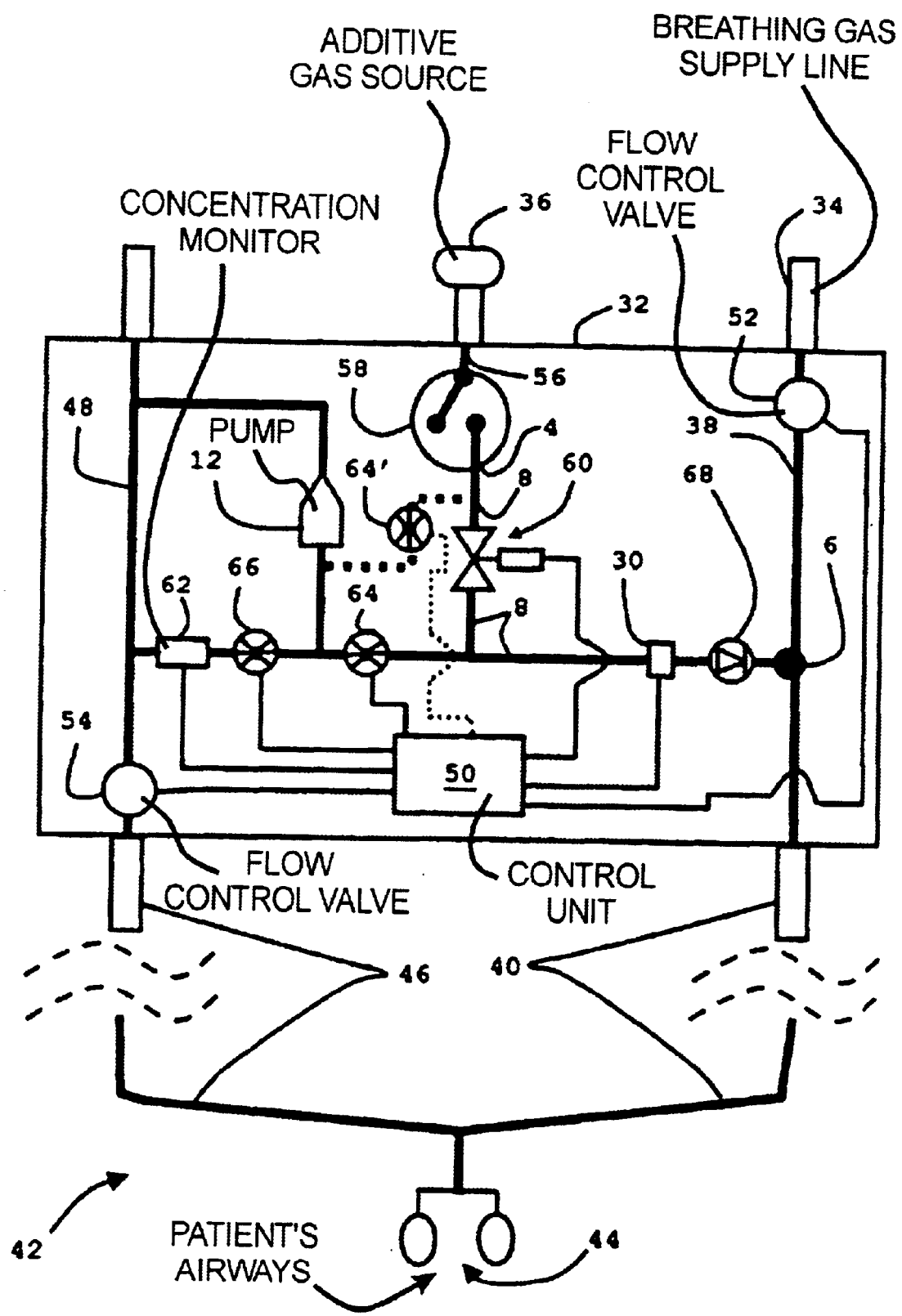
FIG. 2 is a block diagram schematic of a patient breathing arrangement according to the present invention.

Considering now the patient breathing arrangement of FIG. 2 in which elements corresponding with those of the system 2 of FIG. 1 are provided with identical reference numerals and in which the thicker lines represent gas flow paths. A mechanical breathing aid 32, here being a ventilator, is connected to a supply line 34 for breathing gas and to a source 36 of additive gas such as nitrogen monoxide(NO), here shown as a conventional bottled source, for addition into the breathing gas in small, controlled amounts. The breathing aid 32 has an internal inspiration flow path 38 which connects the breathing gas/additive gas mixture to an externally disposed inspiration side 40 of a conventional patient breathing circuit 42, which side 40 will, in use, conduct gas from the breathing aid 32 to a patient's airways 44. An expiration side 46 of the patient breathing circuit 42 is connected to a separate internal expiration flow path 48 of the breathing aid 32 and in use conveys gas from the patient's airways 44 to this internal flow path 48. The breathing arrangement as described above represents a conventional arrangement in which the breathing aid 32 operates in one or more known modes to control the flow of gas to and from a patient. Control of these modes is provided by a known flow control system, here represented generally by a user programmable control unit 50 and an operably connected inspiration flow control valve 52 and expiration flow control valve 54, the operation of which are controlled by the unit 50 to provide a user required breathing mode.

The source of additive gas 36 is connected to an additive gas flow path 56, internally of the breathing aid 32. Connected to this flow path 56 is an on/off valve 58, the operation of which is controlled by the control unit 50 and is arranged so that in the "on" position the source 36 is in gaseous connection with an inlet 4 of a conduit 8 which terminates at an outlet 6 connected to the inspiration flow path 38. An adjustable flow regulator 60, which may be the valving means 10 of FIG. 1, is located in-line with the conduit 8 and is operable to regulate the flow of additive gas from the source 36 into breathing gas in the flow path 38. The regulator 60 is configured with an open position by which a desired flow of additive gas is set and a closed position in which a leakage flow is established and is adjustable in response to a control signal from the flow control unit 50. A pump 12 is connected to extract gas from the conduit 8 at a location either after (as shown) or before (broken line illustration) the regulation means 60, where before and after are relative terms made with reference to the flow direction of additive gas from the source 36 toward the inspiration flow path 38. It will be appreciated that the pump 12 may be connected in a manner to optionally or permanently establish connections at one or both locations using techniques well known in the art. Moreover, as described in relation to the system 2 of FIG. 1, connecting the pump to extract gas at a location before the regulator 60 (broken line illustration) permits the level of residual additive gas to be reduced and even replaced with fresh breathing gas from the supply line 34. This is particularly useful if the additive gas supplied from the source 36 is very reactive and is readily oxidizable to a more harmful gas, such as is the case with NO as additive gas which quickly forms nitrogen dioxide ($NO_2$), as is well known.

The pump 12 is also connected to extract gas from the expiration flow path 48 and through a concentration monitor 62 which is sensitive to and provides an output indicative of the concentration of additive gas in the gas extracted from the expiration flow path 48. This output is passed to the flow control unit 50 which is programmed to control the open position of the flow regulator 60 in dependence of this. A control arrangement, in the form of an adjustable throttle 64 (or 64' if the broken line configuration is employed) is provided to regulate the extraction of the leakage flow from the conduit 8. The throttle 64 is here controlled by the flow control unit 50 in response to a flow signal from a flow meter 30 located to monitor the flow of additive gas through the outlet 6 so that a zero flow into the inspiration flow path 38 prevails when the flow regulation means 60 is in the closed position. A further adjustable throttle 66, here also controlled by the flow control unit 50, may be provided to regulate the extraction of gas from the expiration flow path 48 and also provide additional control over extraction of gas from the conduit 8 (since more or less of the flow through the pump 12 will be from the expiration flow path 48). One or more of these throttles 64 (64') and 66 may be fixed so that a flow at least equal to a maximum expected leakage flow is extracted from the conduit 8. In this case the flow meter 30 may be omitted.

The flow control unit 50 is, in the present embodiment, further configured to control the on/off valve 58 to move to the "off" position (as illustrated in the figure) when the flow regulator 60 is in the closed position to interrupt the supply of additive gas into the conduit 8 from the source 36. In this case then, only the limited amount of gas already present in the conduit 8 can provide the leakage flow through the flow regulator 60. A one-way valve 68 may also be provided and disposed to prevent the pump 12 extracting gas from the inspiration flow path 38.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A fluid flow regulation system comprising:
   an inlet;
   an outlet;
   an adjustable flow regulator connected between said inlet and said outlet for regulating a small fluid flow between said inlet and said outlet, having a closed position at which a leakage fluid flow occurs between said inlet and said outlet;
   a flow meter connected to measure fluid flow from said outlet and which generates a meter output indicative of said fluid flow from said outlet;
   an extraction device in fluid communication with at least one of said inlet and said outlet to extract fluid to produce a flow of at most zero from said outlet when said flow regulator is in said closed position, and
   said extraction device including a control unit connected to said flow meter to regulate extraction of said fluid by said extraction device dependent on said meter output.

2. A fluid flow regulation system as claimed in claim 1 wherein said extraction device has a fluid connection with said inlet, and extracts fluid at a flow at least equal to said leakage flow.

3. A patient breathing arrangement comprising:
   a mechanical breathing aid for controlling a supply of breathing gas to a patient, having an inspiration flow path, an expiration flow path, and an additive gas flow path;
   a patient breathing circuit having an inspiration side for conducting breathing gas from said inspiration flow path toward said patient and an expiration side for conducting gas from said patient to said expiration flow path; and
   a gas flow regulation system having an inlet in fluid communication with said additive gas flow path for receiving additive gas from the additive gas flow path, an outlet in fluid communication with said inspiration side of said breathing circuit for supplying additive gas received from said additive gas flow path to said inspiration side, and an adjustable flow regulator connected between said inlet and said outlet for regulating a small fluid flow between said inlet and said outlet, having a closed position at which a leakage gas flow occurs between said input and said output, a flow meter connected to measure fluid flow from said outlet and which generates a meter output indicative of said fluid flow from said outlet, and having an extraction device in gas flow communication with at least one of said inlet and said outlet, for extracting gas to produce a zero flow from said outlet when said flow regulator is in said closed position, said extraction device including a control unit connected to said flow meter to regulate extraction of said fluid by said extraction device dependent on said meter output.

4. A patient breathing arrangement as claimed in claim 3 further comprising a concentration monitor which identifies a concentration of said additive gas, and wherein said extraction device is connected to said expiration flow path and additionally removes a portion of expiration gas from said expiration flow path for supply to said concentration monitor.

5. A method for regulating a small fluid flow between an inlet and an outlet, comprising the steps of:
   connecting an adjustable flow regulator between the inlet and the outlet for regulating a small fluid flow between the inlet and the outlet, said adjustable flow regulator having a closed position at which a leakage flow occurs between the inlet and the outlet;
   connecting a flow meter to measure fluid from said outlet and generating, with said flow meter, a meter output indicative of said fluid flow from said outlet; and
   connecting an extraction device in fluid communication with at least one of the inlet and the outlet and extracting fluid with said extraction device to produce a flow of at most zero from said outlet when said flow regulator is in said closed position, and regulating extraction of said fluid with said extraction device dependent on said meter output.

* * * * *